(12) United States Patent
Weigel et al.

(10) Patent No.: US 6,239,329 B1
(45) Date of Patent: *May 29, 2001

(54) SHOOT MERISTEM SPECIFIC PROMOTER SEQUENCES

(75) Inventors: Detlef Weigel, Del Mar; Ilha Lee, San Diego, both of CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/265,731

(22) Filed: Mar. 9, 1999

Related U.S. Application Data

(63) Continuation of application No. 08/693,457, filed on Aug. 7, 1996, now Pat. No. 5,880,330.

(51) Int. Cl.[7] .............................. A01H 5/00; C12N 5/10; C12N 15/82
(52) U.S. Cl. .................... 800/278; 800/279; 800/287; 800/294; 800/301; 800/295; 800/317.3; 435/468; 435/469; 435/480; 435/320.1; 536/24.1
(58) Field of Search ................. 435/320.1, 468, 435/469, 480; 536/24.1; 800/278, 279, 287, 294, 301, 295, 317.3

(56) References Cited

U.S. PATENT DOCUMENTS 5,097,025 * 3/1992 Benfey et al. .
5,880,330 * 9/1999 Weigel et al. .

OTHER PUBLICATIONS

Ingram, et al., Parallels between Unusual Floral Organs and Fimbriata, Genes Controlling Flower Development in Arabidopsis and Antirrhinum, The Plant Cell , 7:1501–1510, Sep. 1995.

Medford, et al., Molecular Cloning and Characterization of Genes Expressed in Shoot Apical Meristems, The Plant Cell , 3:359–370, Apr. 1991.

Simon, et al., Fimbriata Controls Flower Development by Mediating between Meristem and Organ Identity Genes, Cell , 78:99–107, 1994.

Weigel, et al., Genetic Hierarchy Controlling Flower Development, Molecular Basis of Morphogenesis pp. 93–107, 1993.

* cited by examiner

*Primary Examiner*—Elizabeth Kemmerer
(74) *Attorney, Agent, or Firm*—Knobbe, Martens, Olson & Bear, LLP

(57) ABSTRACT

A novel tissue-specific promoter is provided which has been isolated from the upstream non-coding region of a plant UFO gene. This promoter, operably associated with a nucleic acid sequence expressing a product of interest, initiates and regulates the transcription of such sequences in a shoot meristem-specific tissue.

21 Claims, 5 Drawing Sheets

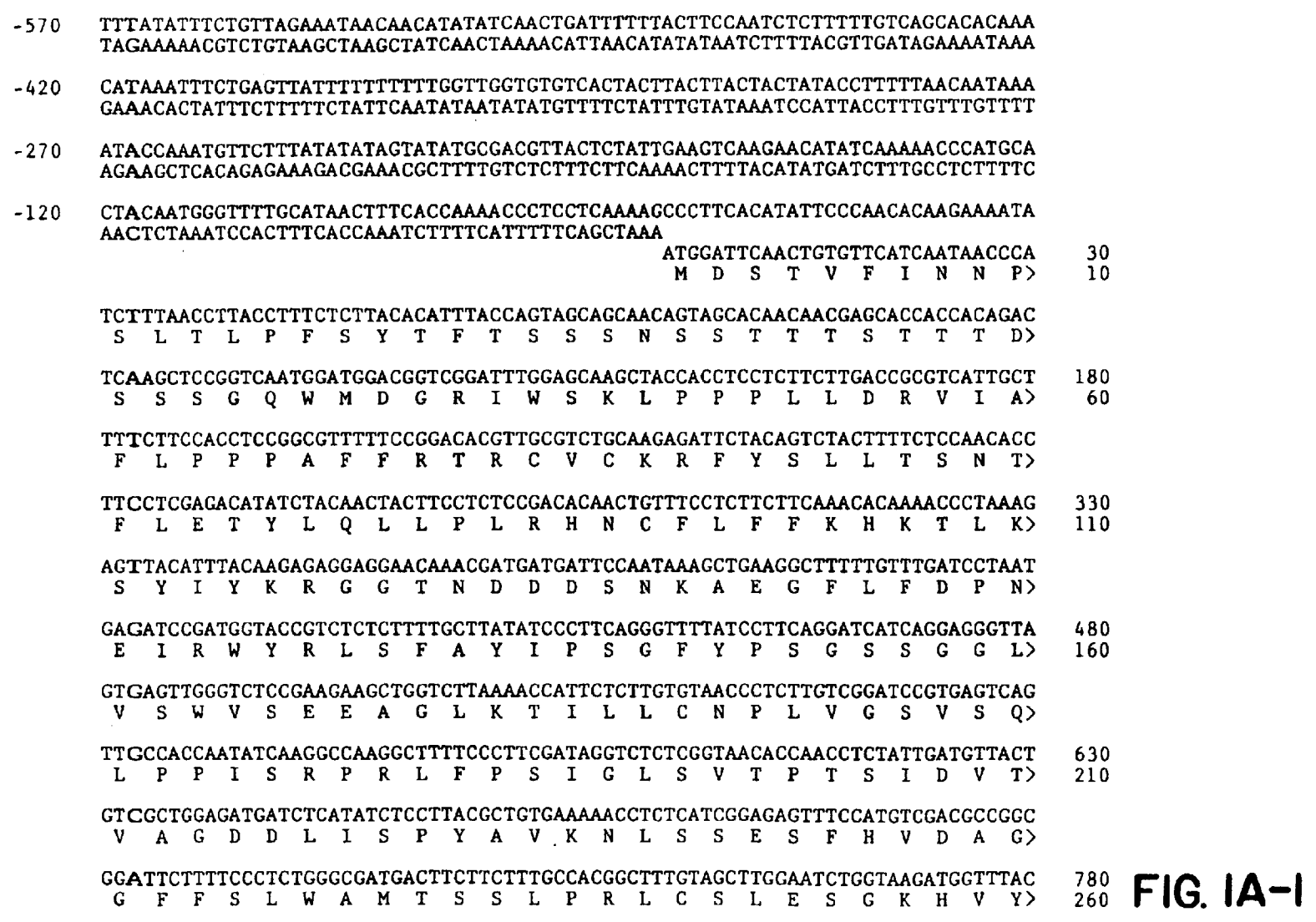

```
GTGCAAGGCAAGTTTTACTGTATGAACTATAGCCCCTTTAGCGTTTTGTCCTATGAAGTTACTGGAAACCGGTGG    930
 V  Q  G  K  F  Y  C  M  N  Y  S  P  F  S  V  L  S  Y  E  V  T  G  N  R  W>   310

ATCAAGATTCAAGCTCCGATGAGGAGATTCTCAGATCTCCAAGCTTGTTAGAGAGCAAAGGGAGGCTTATTCTT
 I  K  I  Q  A  P  M  R  R  F  L  R  S  P  S  L  L  E  S  K  G  R  L  I  L>

GTAGCAGCTGTTGAGAAAAGCAAGTTGAACGTTCCAAAAAGCCTACGACGTTTGGAGTTTGCAACAAGATAACGCC
 V  A  A  V  E  K  S  K  L  N  V  P  K  S  L  R  L  W  S  L  Q  Q  D  N  A>

ACATGGGTCGAGATCGAACGGATGCCTCAGCCGCTCTACACACAGTTTGCAGCAGAAGAAGGTGGAAAAGGATTC   1080
 T  W  V  E  I  E  R  M  P  Q  P  L  Y  T  Q  F  A  A  E  E  G  G  K  G  F>    360

GAGTGTGTCGGAAATCAAGAGTTTGTAATGATTGTGTTAAGAGGAACCTCGTTGCAGTTGCTGTTTGATATAGTG
 E  C  V  G  N  Q  E  F  V  M  I  V  L  R  G  T  S  L  Q  L  L  F  D  I  V>

AGAAAAAGCTGGCTTTGGGTTCCTCCCTGTCCCCCTTACTCCCGGCCAGTGGTGGGGGGAGTGGGGGGTTCAGAC   1230
 R  K  S  W  L  W  V  P  P  C  P  Y  S  G  G  S  G  G  G  S  G  G  G  S  D>    410

GGAGAGGTCTTGCAGGGTTTTGCTTATGACCCGGTTCTTACTACACCCGGTGGTTAGTCTTCTTGATCAGTTAACA
 G  E  V  L  Q  G  F  A  Y  D  P  V  L  T  T  P  V  V  S  L  L  D  Q  L  T

CTTCCATTCCTGAGTCTGTTAG                                                         1329
 L  P  F  F  P  G  V  C  *                                                      442

TTTTTAGACTTTAAGATAAAGAGACTACTGTGTTTCCACTTCTGACGTT                    1380

AAGACTGCTTGTGTTTTCTCAAAATTCTGTTCTTTATCTTATTACTGTCTGTATGTAGTAAGTTTATATTTC
TAATGTCAATGTCTAATCTTTGACAACATGTCAACACATAACAACATACAACAGATTTCTAATTGCCTACAATCCAAT    1530

CCAATCCTAAATCCATCAAACTCAAAAACATAACCCTTGGGAGAATGGTTTCACTTGAGCTTAACCTGGAGAATG
AGATGAACTTTTCTGTTCATTATTGTCTCCTGAGTCTCTTCATTGCCCTCAATTCCTATCCCCTGCAAATTAGCAT     1680
```

```
                                                                      Δufo-3
UFO   MDSTVFINNPSLTLPFSYTFTSSSNSSTTTSTTTDSSSGQWHDGRIWSKLPPPLLDRVIA
FIM   EA---FQT*IFN**LP*G**TTP*TINLQN*MIM*TTNQ**CRQK*II

UFO   FLPPPAFFRTRCVCKRFYSLLFSNTFLETYLQLLPLRNNCFLFFKHKTLKSYIYKRGGTN
FIM   C***********S*S**WI*T**LHAS*I**-*H**QQSI*HHNNNS
                                   stop ufo-4
UFO   DDDSNKAEGFLFDPNEIRWYRLSFAYIPSGFYPSGSSGGLVSWVSEEAGLKTILLCNPLV
FIM   ARPT*-YYQTLKIPLPS*AS**LIC**DS*P*N**S*T UFO   GSVSQLPPISRPRLFPSIGLSVTPTSIDVTVAGDDLISPYAVKNLSSESFHVDAGGFFSL
FIM   NTAI*S-TLEC*T***TI*NS*ISF********T**I*V***Y*I
                          stop ufo-2                              Lufo-6
UFO   WANTSSLPRLGSLESGKMVYVQGKFYCMNYSPFSVLSYEVTGNRWIKIQAPMRRFLRSPS
FIM   *NT*************RH*R************DISL*Q*C************T
                                        stop ufo-5
UFO   LLESKGRLILVAAVEKSKLNVPKSLRLWSLQQDNATWVEIERMPQPLYTQFAAEEGGKGF
FIM   *V***K************AECGTI********QI*EI*R**

UFO   ECVGNQEFVHIVLRGT-SLQLLFDIVRKSWLWVPPCPYSGSGGSSGGGSDGEVLQGFAY
FIM   SAHA**V*LISYDKAVMFC**Q*V*****-*V**DDE-------*H*****

UFO   DPVLTTPVVSLLDQLTLPFPGVC
FIM   E*R*AV*ITP***E*****QSFTA
```

SHOOT MERISTEM SPECIFIC PROMOTER SEQUENCES

This is a continuation of U.S. application Ser. No. 08/693,457, filed Aug. 7, 1996, now U.S. Pat. No. 5,880,330.

STATEMENT AS TO FEDERALLY SPONSORED RESEARCH

This invention was made with Government support under Grant No. IBN-9406948 awarded by the National Science Foundation. The Government has certain rights in this invention.

FIELD OF THE INVENTION

This invention relates generally to plant genetic engineering, and specifically to a tissue specific promoter capable of directing shoot meristem-specific expression.

BACKGROUND OF THE INVENTION

Genes are regulated in an inducible, tissue specific or constitutive manner. There are different types of structural elements which are involved in the regulation of gene expression. Cis-acting elements, located in the proximity of, or within genes, serve to bind sequence-specific DNA binding proteins, i.e., trans-acting factors. The binding of proteins to DNA is responsible for the initiation, maintenance, or down-regulation of gene transcription.

Cis-acting elements which control genes include promoters, enhancers and silencers. Promoters are positioned next to the transcription start site and function in an orientation-dependent manner, while enhancer and silencer elements, which modulate the activity of promoters, may be flexible with respect to their orientation and distance from the transcription start site.

Various promoter sequences are available which may be used in the genetic engineering of plants. Such promoters may be utilized to initiate transcription of a nucleic acid sequence of interest operably linked at the 3' end of the promoter region. Promoters often have transcription specific characteristics such as strength, tissue specificity, developmental stage specificity, etc.

Gene expression in plants may be driven by a number of promoters. Although the endogenous promoter of a gene of interest may be utilized for transcriptional regulation of the gene, the promoter may also be a foreign regulatory sequence. Examples of viral promoters utilized in plant expression vectors include the 35S RNA and 19S RNA promoters of CaMV (Brisson, et al., *Nature*, 310:511, 1984; Odell, et al., *Nature*, 313:810, 1985); the full-length transcript promoter from Figwort Mosaic Virs (FMV) (Gowda, et al., *J Cell Biochem.*, 13D: 301, 1989) and the coat protein promoter of TMV (Takamatsu, et al., *EMBO J* 6:307, 1987). Plant promoters also include the light-inducible promoter from the small subunit of ribulose bis-phosphate carboxylase (ssRUBISCO) (Coruzzi, et al., *EMBO J*, 3:1671, 1984; Broglie, et al., *Science*, 224:838, 1984); mannopine synthase promoter (Velten, et al., *EMBO J*, 3:2723, 1984) nopaline synthase (NOS) and octopine synthase (OCS) promoters (carried on tumor-inducing plasmids of *Agrobacterium tumefaciens*) and heat shock promoters, e.g., soybean hsp17.5-E or hsp17.3-B (Gurley, et al., *Mol. Cell. Biol.*, 6:559, 1986; Severin, et al., *Plant Mol. Biol.*, 15:827, 1990).

Promoters utilized in plant genetic engineering include both constitutive and inducible natural promoters as well as engineered promoters. The CaMV promoters are examples of constitutive promoters. To be useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes.

Examples of inducible promoters useful in plants include those induced by chemical means, such as the yeast metallothionein promoter which is activated by copper ions (Mett, et al., *Proc. Natl. Acad. Sci., U.S.A.*, 90:4567, 1993); In2-1 and In2-2 regulator sequences which are activated by substituted benzenesulfonamides, e.g., herbicide safeners (Hershey, et al, *Plant Mol. Biol.*, 17:679, 1991); and the GRE regulatory sequences which are induced by glucocorticoids (Schena, et al., *Proc. Natl. Acad. Sci., U.S.A.*, 88:10421, 1991).

Tissue specific promoters may also be utilized for expression of genes in plants. Tissue specific promoters useful in transgenic plants include the cdc2a promoter and cyc07 promoter (Ito, et al., *Plant Mol. Biol.*, 24:863, 1994; Martinez, et al, *Proc. Natl. Acad. Sci. USA*, 89:7360, 1992; Medford, et al., *Plant Cell*, 3:359, 1991; Terada, et al., *Plant Journal*, 3:241, 1993; Wissenbach, et al., *Plant Journal*, 4:411, 1993). Additional tissue specific promoters that are utilized in plants include the histone promoter (Atanassova, et al., *Plant Journal*, 2:291, 1992); the cinnamyl alcohol dehydrogenase (CAD) promoter (Feuillet, et al., *Plant Mol. Biol.*, 27:651, 1995); the mustard CHS 1 promoter (Kaiser, et al., *Plant Mol. Biol.*, 28:231, 1995); the bean grp 1.8 promoter (Keller, et al., *Plant Mol. Biol.*, 26:747, 1994); the PAL1 promoter (Ohl, et al., *Plant Cell*, 2:837, 1990); and the chalcone synthase A promoter (*Plant Mol. Biol.*, 15:95–109, 1990).

SUMMARY OF THE INVENTION

The present invention provides a novel tissue-specific promoter isolated from the Unusual Floral Organ gene (UFO). Transgenic plants, in which the invention promoter is fused to a nucleic acid sequence expressing a product of interest, exhibit phenotypes that indicate that the promoter can drive functional expression of a heterologous gene in shoot meristems.

In a first embodiment, the invention provides a nucleic acid construct comprising a non-coding regulatory sequence isolated from a plant Unusual Floral Organs (UFO) gene and a nucleic acid sequence, wherein said nucleic acid sequence expresses a product selected from a protein of interest or antisense RNA, and wherein said nucleic acid sequence is heterologous to the non-coding sequence. The construct is useful for the production of transgenic plants which express a gene of interest in a shoot meristem-specific manner.

In a second embodiment, the invention provides transgenic plant cells comprising the nucleic acid constructs of the invention as well as plants comprising such cells.

In a further embodiment, the invention provides a method of providing increased transcription of a nucleic acid sequence expressing a product selected from a protein of interest or antisense RNA. The method comprises providing a plant having integrated in its genome a nucleic acid construct of the invention and subjecting the plant to conditions suitable for growth.

BRIEF DESCRIPTION OF THE DRAWINGS

FIG. 1A-1 to 1A-2 is the nucleotide (SEQ ID NO: 1) and deduced amino acid sequence (SEQ ID NO: 2) of the UFO gene and some 5' and 3' noncoding sequences.

FIG. 2 is a comparison of UFO (SEQ ID NO: 2) and FIM (SEQ ID NO: 5) protein sequences and location of ufo mutations associated with alleles ufo-2 through ufo-6.

DESCRIPTION OF THE PREFERRED EMBODIMENTS

Figure 3:
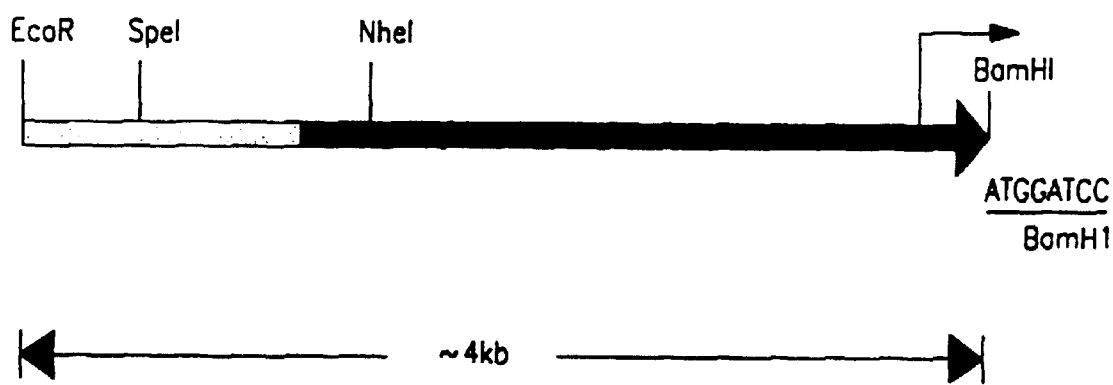
FIG. 3 is a restriction map of the UFO promoter.
Figure 4A:
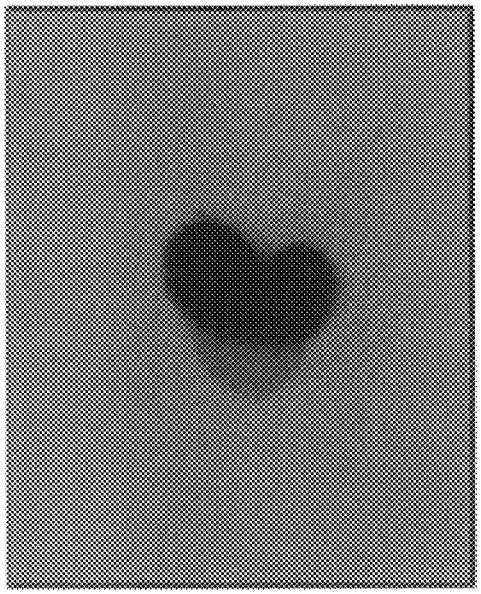
FIGS. 4A–D shows photographs of GUS activity in UFO::GUS transgenic plants during early heart stage (panel A), the torpedo stage (panel B), young seedlings (panel C), and after floral induction (panel D).
Figure 4B:
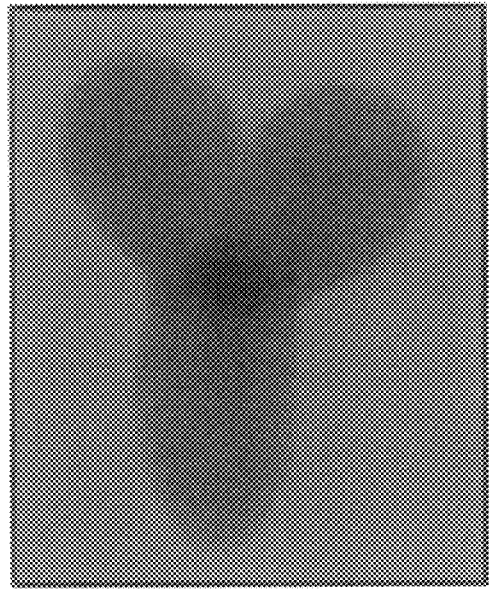
Figure 4C:
Figure 4D:

The present invention provides a novel promoter sequence that is useful for shoot meristem-specific gene expression. The shoot apical meristem forms the primary plant body and often undergoes differentiation to form a flower. In accordance with the present invention, a nucleic acid construct is provided which allows for modification of a plant phenotype based on expression of a desired gene in the shoot meristem. The nucleic acid construct comprises a sequence of interest which provides for the modification in phenotype, positioned downstream from and under the transcriptional initiation regulation of the invention shoot-specific promoter. The shoot meristem-specific promoter is useful for specific expression, in the shoot meristem, of genes involved in regulating development. Such genes include those involved in flowering, as well as genes that protect against pathogens by encoding toxins.

In a first embodiment, the invention provides a nucleic acid construct comprising a non-coding regulatory sequence isolated upstream from a plant Unusual Floral Organs (UFO) gene, wherein the non-coding regulatory sequence is operably associated with a nucleic acid sequence expressing a product selected from a protein of interest or antisense RNA and wherein said nucleic acid sequence is heterologous to said non-coding sequence. The construct includes a transcriptional and translational initiation region and a transcriptional and translational termination region functional in plants. In preparing the construct, the various component nucleic acid sequences may be manipulated, so as to provide for nucleic acid sequences in the proper orientation and in the proper reading frame.

The UFO gene regulatory sequence, or promoter, is located in the non-coding region of the gene and exhibits strong expression in the shoot apical meristem. Approximately 4 kilobases of 5' non-coding sequence was isolated upstream from the coding sequence, as described in the Examples described herein. SEQ ID NO: 3 shows the sequence of approximately 2.6 kb of the 3'-terminal region of the promoter. The main transcription start site is at −225bp relative to the ATG initiation codon. The transcription initiation sequences include transcriptional control regions such as TATAA and CAAT box sequences as well as sequences which regulate the tissue specificity of the transcribed product. In the nucleic acid construct of the invention, the ATG start codon is typically provided by the nucleic acid sequence expressing the product of interest.

One may identify a convenient restriction site in the 5'-untranslated region of the UFO gene and in the 5' region of the nucleic acid sequence expressing the product of interest and employ an adapter which will join the two sequences. Alternatively, one may introduce a polylinker immediately downstream from the UFO noncoding region for insertion of the nucleic acid sequence expressing the product of interest.

Placing a nucleic acid sequence expressing a product of interest under the regulatory control of a promoter or a regulatory element means positioning the sequence such that expression is controlled by the promoter or regulatory element. In general, promoters are positioned upstream of the genes that they control. Thus, in the construction of promoter/gene combinations, the promoter is preferably positioned upstream of the gene and at a distance from the transcription start site that approximates the distance between the promoter and the gene it controls in its natural setting. As is known in the art, some variation in this distance can be tolerated without loss of promoter function. Similarly, the preferred positioning of a regulatory element with respect to a gene placed under its control reflects its natural position relative to the structural gene it naturally regulates. Again, as is known in the art, some variation in this distance can be accommodated. The 5'-noncoding sequences which are used in the invention construct are not more than about 4 kbp in length.

Promoter function during expression of a gene under its regulatory control can be tested at the transcriptional stage using DNA/RNA and RNA/RNA hybridization assays (in situ hybridization) and at the translational stage using specific functional assays for the protein synthesized (for example, by enzymatic activity or by immunoassay of the protein).

As used herein, the term "nucleic acid sequence" refers to a polymer of deoxyribonucleotides or ribonucleotides, in the form of a separate fragment or as a component of a larger construct. Nucleic acids expressing the products of interest can be assembled from cDNA fragments or from oligonucleotides which provide a synthetic gene which is capable of being expressed in a recombinant transcriptional unit. Polynucleotide or nucleic acid sequences of the invention include DNA, RNA and cDNA sequences.

Nucleic acid sequences utilized in the invention can be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR). Sequences for specific genes can also be found in GenBank, National Institutes of Health computer database.

The phrase "nucleic acid sequence expressing a product of interest" refers to a structural gene which expresses a product selected from a protein of interest or antisense RNA. The term "structural gene" excludes the non-coding regulatory sequence which drives transcription. The structural gene may be derived in whole or in part from any source known to the art, including a plant, a fungus, an animal, a bacterial genome or episome, eukaryotic, nuclear or plasmid DNA, cDNA, viral DNA or chemically synthesized DNA. A structural gene may contain one or more modifications in either the coding or the untranslated regions which could affect the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns, bound by the appropriate splice junctions. The structural gene may also encode a fusion protein. It is contemplated that introduction into plant tissue of nucleic acid constructs of the invention will include constructions wherein the structural gene and its promoter e.g., UFO promoter, are each derived from different plant species.

The term "heterologous nucleic acid sequence" as used herein refers to at least one structural gene which is operably associated with the regulatory sequence or promoter of the invention. The nucleic acid sequence originates in a foreign species, or, in the same species if substantially modified from its original form. For example, the term "heterologous nucleic acid sequence" includes a nucleic acid originating in the same species, where such sequence is operably linked to a promoter that differs from the natural or wild-type promoter (e.g., UFO promoter).

The term "operably associated" refers to functional linkage between the promoter sequence and the structural gene regulated by the promoter sequence. The operably linked promoter controls the expression of the product expressed by the structural gene.

Examples of structural genes that may be employed in the present invention include the *Bacillus thuringiensis* toxin gene, which provides pest/pathogen protection and the LEAFY gene, which controls flowering in plants. A variety of structural genes of interest that can be operably linked to the promoter of the invention are available. For example, various sequences may be employed relating to enhanced resistance to pesticides. Such sequences provide for the expression of a protein toxin derived from, for example, *Bacillus thuringiensis*. Moreover, sequences relating to herbicides may also be employed. Such sequences can provide for the expression of a mutated 5-enolpyruvyl-2-phosphoshikimate synthase to provide decreased sensitivity to glyphosate. Such sequences can also provide for the expression of a gene product involved in detoxification of bromoxynil. Sequences may also be employed relating to enhanced resistance to stress (such as provided by a gene for superoxide dismutase), temperature changes, osmotic pressure changes and salinity (such as a gene associated with the overproduction of proline) and the like. Growth of the shoot meristem may be modulated, either increased or decreased, depending on the particular need. Antisense sequences may be used to reduce growth or other phenotypic traits.

The term "genetic modification" or "genetically modified" as used herein refers to the introduction of one or more heterologous nucleic acid sequences into one or more plant cells, which can generate whole, sexually competent, viable plants. The term "genetically modified" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants. Plant cells include cells in plants as well as protoplasts in culture. Accordingly, a seed comprising multiple plant cells capable of regenerating into a whole plant, is included in the definition of "plant cell". Plant tissue includes differentiated and undifferentiated tissue derived from roots, shoots, pollen, seeds, tumor tissue, such as crown galls, and various forms of aggregations of plant cells in culture, such as embryos and calluses.

As used herein, the term "plant" refers to either a whole plant, a plant part, a plant cell, or a group of plant cells, such as plant tissue, for example. Plantlets are also included within the meaning of "plant". Plants included in the invention are any plants amenable to transformation techniques, including angiosperms, gymnosperms, monocotyledons and dicotyledons.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beats, eggplant, spinach, cucumber, squash, melons, cantaloupe, sunflowers and various ornamentals. Woody species include poplar, pine, sequoia, cedar, oak, etc.

Genetically modified plants of the present invention are produced by contacting a plant cell with an invention nucleic acid construct as described above. The construct is preferably contained within a vector. Vector(s) employed in the present invention for transformation of a plant cell for shoot meristem expression comprise a nucleic acid sequence comprising at least one structural gene expressing a product of interest, operably associated with the promoter of the invention. It is preferred that the vector harboring the heterologous nucleic acid sequence also contain one or more selectable marker genes so that the transformed cells can be selected from non-transformed cells in culture, as described herein.

As used herein, the term "marker" refers to a gene encoding a trait or a phenotype which permits the selection of, or the screening for, a plant or plant cell containing the marker. Preferable, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-beta-phosphotransferase, thymidine kinase, exanthineguanine phospho-ribosyltransferase and aminoglycoside 3'-O-phosphotransferase II. Other suitable markers will be known to those of skill in the art.

To commence a transformation process in accordance with the present invention, it is first necessary to construct a suitable vector and properly introduce it into the plant cell. The details of the construction of the vectors then utilized herein are known to those skilled in the art of plant genetic engineering.

For example, the nucleic acid sequences utilized in the present invention can be introduced into plant cells using Ti plasmids, root-inducing (Ri) plasmids, and plant virus vectors. (For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9, and Horsch, et al., *Science*, 227:1229, 1985, both incorporated herein by reference).

One of skill in the art will be able to select an appropriate vector for introducing the invention nucleic acid construct in a relatively intact state. Thus, any vector which will produce a plant carrying the introduced nucleic acid construct should be sufficient. Even a naked piece of nucleic acid would be expected to be able to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, Methods of Enzymology, Vol. 153, 1987, Wu and Grossman, Eds., Academic Press, incorporated herein by reference). As used herein, the term "transformation" means alteration of the genotype of a host plant by the introduction of a nucleic acid construct as described herein.

For example, a construct of the invention can be introduced into a plant cell utilizing *Agrobacterium tumefaciens* containing the Ti plasmid. In using an *A. tumefaciens* culture as a transformation vehicle, it is most advantageous to use a non-oncogenic strain of the Agrobacterium as the vector carrier so that normal non-oncogenic differentiation of the transformed tissues is possible. It is also preferred that the Agrobacterium harbor a binary Ti plasmid system. Such a binary system comprises 1) a first Ti plasmid having a virulence region essential for the introduction of transfer DNA (T-DNA) into plants, and 2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells (De Framond, *Biotechnology*, 1:262, 1983; Hoekema, et al., *Nature*, 303:179, 1983). Such a binary system is preferred because it does not require integration into Ti plasmid in Agrobacterium.

Methods involving the use of Agrobacterium include, but are not limited to: 1) co-cultivation of Agrobacterium with cultured isolated protoplasts; 2) transformation of plant cells or tissues with Agrobacterium; or 3) transformation of seeds, apices or meristems with Agrobacterium.

In addition, gene transfer can be accomplished by in situ transformation by Agrobacterium, as described by Bechtold, et al., (*C.R. Acad. Sci. Paris*, 316:1194, 1993) and exemplified in the Examples herein. This approach is based on the vacuum infiltration of a suspension of Agrobacterium cells.

The preferred method of introducing a nucleic acid construct of the invention into plant cells is to infect such plant cells, an explant, a meristem or a seed, with transformed *Agrobacterium tumefaciens* as described above. Under appropriate conditions known in the art, the transformed plant cells are grown to form shoots, roots, and develop further into plants.

Alternatively, a nucleic acid construct of the invention can be introduced into a plant cell by contacting the plant cell using mechanical or chemical means. For example, the nucleic acid can be mechanically transferred by microinjection directly into plant cells by use of micropipettes. Alternatively, the nucleic acid may be transferred into the plant cell by using polyethylene glycol which forms a precipitation complex with genetic material that is taken up by the cell.

A nucleic acid construct of the invention can also be introduced into plant cells by electroporation (Fromm, et al, *Proc. Natl. Acad. Sci., U.S.A.,* 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing-nucleic acid into a plant cell is high velocity ballistic penetration by small particles with the nucleic acid to be introduced contained either within the matrix of small beads or particles, or on the surface thereof (Klein, et al., *Nature* 327:70, 1987). Although, typically only a single introduction of a new nucleic acid sequence is required, this method particularly provides for multiple introductions.

Cauliflower mosaic virus (CaMV) may also be used as a vector for introducing a nucleic acid construct of the invention into plant cells (U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

In another embodiment, the invention affords a method of providing increased transcription of a nucleic acid sequence expressing a product of interest in shoot meristem tissue. The method comprises providing a plant having integrated into its genome a nucleic acid construct of the invention and subjecting the plant to conditions suitable for growth whereby transcription of the nucleic acid sequence is increased in the shoot meristem tissue.

Typically, the nucleic acid construct is introduced into a plant cell by contacting the cell with a vector containing the promoter-nucleic acid sequence encoding the protein of interest construct. As used herein, the term "contacting" refers to any means of introducing the vector(s) into the plant cell, including chemical and physical means as described above. Preferably, contacting refers to introducing the nucleic acid or vector into plant cells (including an explant, a meristem or a seed), via *Agrobacterium tumefaciens* transformed with the heterologous nucleic acid as described above.

Normally, a plant cell is regenerated to obtain a whole plant from the transformation process. The immediate product of the transformation is referred to as "transgenote". The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension, to the stage of ripening and germination as natural embryos. The culture media will generally contain various amino acids and hormones, necessary for growth and regeneration. Examples of hormones utilized include auxin and cytokinins. It is sometimes advantageous to add glutamic acid and proline to the medium, especially for such species as corn and alfalfa. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration. (see *Methods in Enzymology*, Vol. 118 and Klee, et al., *Annual Review of plant Physiology*, 38:467, 1987). Utilizing the leaf disk-transformation-regeneration method of Horsch, et al., *Science*, 227:1229, 1985, disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by the taking of cuttings or by tissue culture techniques to produce multiple identical plants. Selection of desirable transgenotes is made and new varieties are obtained and propagated vegetatively for commercial use.

In seed propagated crops, the mature transgenic plants can be self crossed to produce a homozygous inbred plant. The inbred plant produces seed containing the newly introduced foreign gene(s). These seeds can be grown to produce plants that would produce the selected phenotype, e.g. early flowering.

Parts obtained from the regenerated plant, such as flowers, seeds, leaves, branches, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

The invention includes a plant produced by the method of the invention, including plant tissue, seeds, and other plant cells derived from the genetically modified plant.

The above disclosure generally describes the present invention. A more complete understanding can be obtained by reference to the following specific examples which are provided herein for purposes of illustration only and are not intended to limit the scope of the invention.

EXAMPLES

Meristems in the aerial portion of a plant have to choose between two alternative fates, shoot or flower meristem, a decision that is regulated by a set of meristem-identity genes (Weigel, D., *Annu. Rev. Genetics*, 22:19, 1995). Such genes include the snapdragon gene FIMBRIATA (FIM) whose inactivation causes a partial transformation of flowers into shoots (Simon, et al., *Cell*, 78:99, 1994). The FIM gene has been cloned and shown to be specifically expressed in young flowers (Simon, et al., supra). A gene with significant sequence similarity to FIM has been isolated from *Arabidopsis thaliana* and shown to correspond to the UFO gene, mutations in which cause phenotypes similar to that of mutations in FIM (Ingraham; et al., *Plant Cell*, 7:1501, 1995; Levin and Meyerowitz, *Plant Cell*, 7:529, 1995; Wilkinson an Haughn, *Plant Cell*, 7:1485, 1995).

The present invention describes isolation of the UFO coding and noncoding nucleic acid sequences. UFO RNA was found to be expressed not only in flowers as previously reported (Ingram, et al., supra), but also in shoot meristems. To test whether the UFO promoter is sufficient to drive expression of a heterologous gene, the promoter was fused to the structural gene β-glucuronidase (GUS). Transgenic Arabidopsis and tobacco plants that carry a fusion of the UFO promoter to a reporter gene encoding β-glucuronidase (GUS) were constructed. These plants express high levels of GUS in shoot meristems, as determined by histochemical staining with the GUS substrate X-gluc (5-bromo4-chloro-3-indoyl β-D-glucuronide). Functional activity of the UFO promoter in shoot meristems was confirmed by generating transgenic Arabidopsis plants in which the UFO promoter is fused to the nucleic acid sequence encoding the protein of interest encoding the LEAFY (LFY) gene product. High levels of LFY expression are normally restricted to young flowers (Weigel, et al., *Cell*, 69:843, 1992), and transgenic plants in which LFY is constitutively expressed show transformation of shoots into flowers, apparently due to ecotopic expression of LFY in shoot meristems (Weigel and Nilsson, *Nature*, 377:495, 1995). A similar phenotype is observed in UFO::LFY plants, indicating that the UFO promoter can drive functional expression of a heterologous gene in shoot meristems.

Example 1

Isolation and Identification of the UFO Gene

The UFO gene was isolated using probes for the snapdragon FIM gene. Genomic DNA was extracted from locally purchased snapdragons, and two adjacent portions of the FIM coding region were amplified by polymerase chain (PCR) reaction (Saiki, et a., *Science*, 239:487, 1988; Simon, et al., supra). The PCR products were radioactively labeled and used to screen a lambda vector library of Arabidopsis genomic DNA. Duplicate filters were hybridized with the non-overlapping FIM probes, and clones that hybridized to both probes were purified (Sambrook, et al., *Molecular Cloning*, 2nd Edition, Cold Spring Harbor: Cold Spring Harbor Laboratory, 1989). The FIM cross-hybridizing region was subcloned into plasmid vectors (pBluescript, Stratagene) and the DNA sequence was determined by the Sanger method (Sambrook, et al., supra.) (FIG. 1A). Analysis of the genomic sequence identified an uninterrupted open reading frame of 1326 base pairs, with coding potential for a 442 amino acid long protein that shares significant similarity with the FIM protein (FIG. 2).

To confirm that this gene corresponded to UFO, a CAPS marker (Konieczny and Ausubel, *Plant J.*, 4:403, 1993) was developed and the map position of the gene determined by mapping it against a previously characterized set of recombinant inbred lines (Lister and Dean, *Plant J.*, 4:745, 1993). The derived map position at 68 cM on chromosome I agrees with the genetic linkage of ufo mutations to the CAL locus on chromosome I (Levin and Meyerowitz, supra). Genomic DNA was extracted from five is ufo mutant alleles, ufo-2 through ufo-6 (Levin and Meyerowitz, supra), and the UFO coding region was amplified by PCR (Saiki, et al., supra). Sequencing revealed single amino acid changes in all five alleles (FIG. 2). The four strong alleles ufo-2 through ufo-5 are all associated with nonsense mutations predicted to cause a truncation of the UFO protein. The weak allele ufo-6 has a missense mutation. The map position together with the mutant sequences showed that this clone was derived from the UFO gene. Further confirmation was obtained by complementation of the ufo-2 mutations with a transgene in which the UFO coding region is under the control of the 35S promoter from cauliflower mosaic virus. This promoter is described in Odell, et al., *Nature*, 313:810, 1985. These results agree with the results reported by Ingraham, et al., (1995 coding region; GenBank database, accession number X89224).

Example 2

Analysis of UFO Expression and Promoter Sequences

Using in situ hybridization to sections of Arabidopsis plants, the UFO gene was found to be expressed in shoot meristems as well as in young flowers. To study the activity of the UFO promoter, approximately 4 kb of upstream sequences were fused to the GUS reporter (Jefferson, et al., supra). In brief, a BamHI restriction site was introduced downstream of the initiation codon, to produce the sequence ATGGATcC (initiation codon indicated in bold, mutated nucleotide indicated by lower case letter).

The 5' fragment used extends from an EcoRI site to this artificial BamHI site (FIG. 3). The fragment was cloned as an HindIII/BamHI fragment upstream of the GUS coding region in the backbone of the pCGN 1547 T-DNA transformation vector (McBride and Summerfelt, *Plant Mol. Biol.*, 14:269, 1990), yielding pDW228, which was transformed into *Agrobacterium tumefaciens* strain, ASE (Fraley, et al. *Biotechnology*, 3:629, 1985), and introduced in to *Arabidopsis thaliana* ecotype Columbia plants by the vacuum infiltration method (Bechtold, et al., *C.R. Acad. Sci.*, 316:1194, 1993). Transgenic plants were selected on kanamycin, seeds were harvested, and progeny were analyzed for GUS activity using the X-gluc substrate at various times during development (Jefferson, et al., *EMBO J.*, 6:3901, 1987).

Strong expression of GUS was first detected in the apical part of the embryo during early heart stage (FIG. 4, panel A). As the shoot apical meristems forms during the torpedo stage, GUS activity becomes restricted to the shoot apical meristem (FIG. 4, panel B). In young seedlings that are not florally induced, the same pattern was detected (FIG. 4, panel C). Once floral induction has occurred, GUS activity is detected in the shoot apical meristem and in young flowers (FIG. 4, panel D). GUS activity is also detected in axillary shoot meristems that form in the axils of rosette leaves.

The foregoing is meant to illustrate, but not to limit, the scope of the invention. Indeed, those of ordinary skill in the art can readily envision and produce further embodiments, based on the teachings herein, without undue experimentation.

What is claimed is:

1. An isolated nucleotide sequence, comprising a promoter sequence operably associated with a heterologous nucleotide sequence, wherein said promoter sequence comprises a fragment of SEQ ID NO: 3 and specifically drives expression of said heterologous nucleotide sequence in shoot meristems.

2. The isolated nucleotide sequence of claim 1, further comprising a transcriptional and translational initiation region.

3. The isolated nucleotide sequence of claim 1, further comprising a transcriptional termination region functional in a plant cell.

4. The isolated nucleotide sequence of claim 1, wherein said heterologous nucleotide sequence encodes a *Bacillus thuringiensis* toxin.

5. The isolated nucleotide sequence of claim 1, wherein said heterologous nucleotide sequence encodes the LEAFY gene product.

6. A transgenic plant cell comprising a promoter sequence operably associated with a heterologous nucleotide sequence, wherein said promoter sequence comprises a fragment of SEQ ID NO: 3 and specifically drives expression of said heterologous nucleotide sequence in a shoot meristem cell.

7. The transgenic plant cell of claim 6, wherein said transgenic plant cell is a tobacco plant cell.

8. The transgenic plant cell of claim 6, wherein said transgenic plant cell is an Arabidopsis plant cell.

9. The transgenic plant cell of claim 6, further comprising a selectable marker.

10. A transgenic plant comprising a promoter sequence operably associated with a heterologous nucleotide sequence, wherein said promoter sequence comprises a fragment of SEQ ID NO: 3 and specifically drives expression of said heterologous nucleotide sequence in shoot meristem tissue.

11. The transgenic plant of claim 10, wherein said transgenic plant is a tobacco plant.

12. The transgenic plant of claim 10, wherein said transgenic plant is an *Arabidopsis thaliana* plant.

13. The transgenic plant of claim 10, further comprising a selectable marker.

14. An expression vector comprising a promoter sequence operably associated with a heterologous nucleotide sequence, wherein said promoter sequence comprises a fragment of SEQ ID NO: 3 and specifically drives expression of said heterologous nucleotide sequence in shoot meristems.

15. The expression vector of claim 14, wherein said expression vector is selected from the group consisting of: a retroviral vector, a Ti plasmid and Cauliflower mosaic virus (CaMV).

16. The expression vector of claim 14, wherein said expression vector comprises a nucleotide sequence encoding a selectable marker.

17. A method of providing increased transcription of a nucleic acid sequence in shoot meristem tissue of a plant, said method comprising:

transforming a plant with a nucleic acid construct comprising a promoter sequence operably associated with a heterologous nucleotide sequence, wherein said promoter sequence comprises a fragment of SEQ ID NO: 3 and specifically drives expression of said heterologous nucleotide sequence in shoot meristems detecting increased expression of said heterologous nucleotide sequence.

18. The method of claim 17, wherein said transforming a plant comprises transforming an *Arabidobsis thaliana* plant.

19. The method of claim 17, wherein said transforming a plant comprises transforming a tobacco plant.

20. The method of claim 17, wherein said transforming a plant comprises transforming said plant with *Agrobacterium tumefaciens*.

21. The method of claim 17, wherein said heterologous nucleic acid sequence encodes a *Bacillus thuringiensis* toxin.

* * * * *

UNITED STATES PATENT AND TRADEMARK OFFICE
CERTIFICATE OF CORRECTION

PATENT NO.     : 6,239,329 B1
DATED          : May 29, 2001
INVENTOR(S)    : Detlef Weigel, Ilha Lee It is certified that error appears in the above-identified patent and that said Letters Patent is hereby corrected as shown below:

Column 26,
Line 19, shown as "meristems" should read -- meristems; and --

Signed and Sealed this

Twenty-sixth Day of March, 2002

Attest:

JAMES E. ROGAN
Attesting Officer — Director of the United States Patent and Trademark Office

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
        (A) LENGTH: 3139 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 571..1900

(xi) SEQUENCE DESCRIPTION: SEQ ID NO: 1:

```
TTTATATTTC TGTTAGAAAT AACAACATAT ATCAACTGAT TTTTTACTTC CAATCTCTTT      60

TTGTCAGCAC ACAAATAGAA AAACGTCTGT AAGCTAAGCT ATCAACTAAA ACATTAACAT     120

ATATAATCTT TTACGTTGAT AGAAAATAAA CATAAATTTC TGAGTTATTT TTTTTTTGGT     180

TGGTGTGTCA CTACTTACTT ACTACTATAC CTTTTTAACA ATAAAGAAAC ACTATTTCTT     240

TTTCTATTCA ATATAATATA TGTTTTCTAT TTGTATAAAT CCATTACCTT TGTTTGTTTT     300

ATACCAAATG TTCTTTATAT ATAGTATATG CGACGTTACT CTATTGAAGT CAAGAACATA     360

TCAAAAACCC ATGCAAGAAG CTCACAGAGA AAGACGAAAC GCTTTTGTCT CTTTCTTCAA     420

AACTTTTACA TATGATCTTT GCCTCTTTTC CTACAATGGG TTTTGCATAA CTTTCACCAA     480

AACCCTCCTC AAAAGCCCTT CACATATTCC CAACACAAGA AAATAAACTC TAAATCCACT     540

TTCACCAAAT CTTTTCATTT TTCAGCTAAA ATG GAT TCA ACT GTG TTC ATC AAT     594
                                 Met Asp Ser Thr Val Phe Ile Asn
                                   1               5

AAC CCA TCT TTA ACC TTA CCT TTC TCT TAC ACA TTT ACC AGT AGC AGC     642
Asn Pro Ser Leu Thr Leu Pro Phe Ser Tyr Thr Phe Thr Ser Ser Ser
     10                  15                  20

AAC AGT AGC ACA ACA ACG AGC ACC ACC ACA GAC TCA AGC TCC GGT CAA     690
Asn Ser Ser Thr Thr Thr Ser Thr Thr Thr Asp Ser Ser Ser Gly Gln
 25                  30                  35                  40

TGG ATG GAC GGT CGG ATT TGG AGC AAG CTA CCA CCT CCT CTT CTT GAC     738
Trp Met Asp Gly Arg Ile Trp Ser Lys Leu Pro Pro Pro Leu Leu Asp
                 45                  50                  55

CGC GTC ATT GCT TTT CTT CCA CCT CCG GCG TTT TTC CGG ACA CGT TGC     786
Arg Val Ile Ala Phe Leu Pro Pro Pro Ala Phe Phe Arg Thr Arg Cys
             60                  65                  70

GTC TGC AAG AGA TTC TAC AGT CTA CTT TTC TCC AAC ACC TTC CTC GAG     834
Val Cys Lys Arg Phe Tyr Ser Leu Leu Phe Ser Asn Thr Phe Leu Glu
         75                  80                  85

ACA TAT CTA CAA CTA CTT CCT CTC CGA CAC AAC TGT TTC CTC TTC TTC     882
Thr Tyr Leu Gln Leu Leu Pro Leu Arg His Asn Cys Phe Leu Phe Phe
```

-continued

|  |  |  | 90 |  |  |  | 95 |  |  |  | 100 |  |  |  |
|---|---|---|---|---|---|---|---|---|---|---|---|---|---|---|
| AAA | CAC | AAA | ACC | CTA | AAG | AGT | TAC | ATT | TAC | AAG | AGA | GGA | GGA | ACA | AAC | 930 |
| Lys | His | Lys | Thr | Leu | Lys | Ser | Tyr | Ile | Tyr | Lys | Arg | Gly | Gly | Thr | Asn |
| 105 |  |  |  |  | 110 |  |  |  |  | 115 |  |  |  |  | 120 |

```
      AAA CAC AAA ACC CTA AAG AGT TAC ATT TAC AAG AGA GGA GGA ACA AAC          930
      Lys His Lys Thr Leu Lys Ser Tyr Ile Tyr Lys Arg Gly Gly Thr Asn
      105             110             115             120

GAT GAT GAT TCC AAT AAA GCT GAA GGC TTT TTG TTT GAT CCT AAT GAG          978
      Asp Asp Asp Ser Asn Lys Ala Glu Gly Phe Leu Phe Asp Pro Asn Glu
                          125             130             135

ATC CGA TGG TAC CGT CTC TCT TTT GCT TAT ATC CCT TCA GGG TTT TAT         1026
      Ile Arg Trp Tyr Arg Leu Ser Phe Ala Tyr Ile Pro Ser Gly Phe Tyr
                  140             145             150

CCT TCA GGA TCA TCA GGA GGG TTA GTG AGT TGG GTC TCC GAA GAA GCT         1074
      Pro Ser Gly Ser Ser Gly Gly Leu Val Ser Trp Val Ser Glu Glu Ala
              155             160             165

GGT CTT AAA ACC ATT CTC TTG TGT AAC CCT CTT GTC GGA TCC GTG AGT         1122
      Gly Leu Lys Thr Ile Leu Leu Cys Asn Pro Leu Val Gly Ser Val Ser
          170             175             180

CAG TTG CCA CCA ATA TCA AGG CCA AGG CTT TTC CCT TCG ATA GGT CTC         1170
      Gln Leu Pro Pro Ile Ser Arg Pro Arg Leu Phe Pro Ser Ile Gly Leu
      185             190             195             200

TCG GTA ACA CCA ACC TCT ATT GAT GTT ACT GTC GCT GGA GAT GAT CTC         1218
      Ser Val Thr Pro Thr Ser Ile Asp Val Thr Val Ala Gly Asp Asp Leu
                          205             210             215

ATA TCT CCT TAC GCT GTG AAA AAC CTC TCA TCG GAG AGT TTC CAT GTC         1266
      Ile Ser Pro Tyr Ala Val Lys Asn Leu Ser Ser Glu Ser Phe His Val
                  220             225             230

GAC GCC GGC GGA TTC TTT TCC CTC TGG GCG ATG ACT TCT TCT TTG CCA         1314
      Asp Ala Gly Gly Phe Phe Ser Leu Trp Ala Met Thr Ser Ser Leu Pro
              235             240             245

CGG CTT TGT AGC TTG GAA TCT GGT AAG ATG GTT TAC GTG CAA GGC AAG         1362
      Arg Leu Cys Ser Leu Glu Ser Gly Lys Met Val Tyr Val Gln Gly Lys
          250             255             260

TTT TAC TGT ATG AAC TAT AGC CCT TTT AGC GTT TTG TCC TAT GAA GTT         1410
      Phe Tyr Cys Met Asn Tyr Ser Pro Phe Ser Val Leu Ser Tyr Glu Val
      265             270             275             280

ACT GGA AAC CGG TGG ATC AAG ATT CAA GCT CCG ATG AGG AGA TTT CTC         1458
      Thr Gly Asn Arg Trp Ile Lys Ile Gln Ala Pro Met Arg Arg Phe Leu
                          285             290             295

AGA TCT CCA AGC TTG TTA GAG AGC AAA GGG AGG CTT ATT CTT GTA GCA         1506
      Arg Ser Pro Ser Leu Leu Glu Ser Lys Gly Arg Leu Ile Leu Val Ala
                  300             305             310

GCT GTT GAG AAA AGC AAG TTG AAC GTT CCC AAA AGC CTA CGA CTT TGG         1554
      Ala Val Glu Lys Ser Lys Leu Asn Val Pro Lys Ser Leu Arg Leu Trp
              315             320             325

AGT TTG CAA CAA GAT AAC GCC ACA TGG GTC GAG ATC GAA CGG ATG CCT         1602
      Ser Leu Gln Gln Asp Asn Ala Thr Trp Val Glu Ile Glu Arg Met Pro
          330             335             340

CAG CCG CTC TAC ACA CAG TTT GCA GCA GAA GAA GGT GGA AAA GGA TTC         1650
      Gln Pro Leu Tyr Thr Gln Phe Ala Ala Glu Glu Gly Gly Lys Gly Phe
      345             350             355             360

GAG TGT GTC GGA AAT CAA GAG TTT GTA ATG ATT GTG TTA AGA GGA ACC         1698
      Glu Cys Val Gly Asn Gln Glu Phe Val Met Ile Val Leu Arg Gly Thr
                          365             370             375

TCG TTG CAG TTG CTG TTT GAT ATA GTG AGA AAA AGC TGG CTG TGG GTC         1746
      Ser Leu Gln Leu Leu Phe Asp Ile Val Arg Lys Ser Trp Leu Trp Val
                  380             385             390

CCA CCG TGT CCT TAC TCC GGC AGT GGT GGC GGT AGC TCA GGT GGC GGT         1794
      Pro Pro Cys Pro Tyr Ser Gly Ser Gly Gly Gly Ser Ser Gly Gly Gly
              395             400             405

TCA GAC GGA GAG GTC TTG CAG GGT TTT GCT TAT GAC CCG GTG CTT ACT         1842
```

```
Ser Asp Gly Glu Val Leu Gln Gly Phe Ala Tyr Asp Pro Val Leu Thr
    410                 415                 420

ACA CCG GTG GTT AGT CTT CTT GAT CAG TTA ACA CTT CCA TTT CCT GGA      1890
Thr Pro Val Val Ser Leu Leu Asp Gln Leu Thr Leu Pro Phe Pro Gly
425                 430                 435                 440

GTC TGT TAG T TTTTAGACTT TAAGATAAAG AGACTACTTG TGGTTTCCAC             1940
Val Cys *

TTCTGACGTT AAGACTGCTT GTTGTTTTCT CAAAATTCTG TTTCTTTTAT CTTATTACTG    2000

TCTGTATGTA GTAAGTTTAT ATTTCTAATG TCAAATGTCT AATCTTTGAC AACATGTCAA    2060

CAACATATAC AGACAGATTT CTAATTGCGT ACAATCCAAT CCAATCCTAA ATCCATCAAA    2120

CTCAAAAACA TAACCCTTGG GAGAATGGTT TCACTTGAGC TTAACCTGGA GAATGAGATG    2180

AACTTTTCTG TTCATTATTC TCCTGAGTTC TTCATTGGCC TCAATTCCTA TCCTCCTGCA    2240

AAATTAGCAT CAACATAAGA TCATCCTTGA GTCATTGATT AGTCAAAAGA ATGAATTATG    2300

ACCGATCTTG TATGCTCTTA CCCGATCTTG CAACCGCCCT TGCCTACAAG AATCTTGCGT    2360

TGGCTAAGTT TAGGAGTGAT GAGATGCTGT TCAATTCTAA GAGACCCGTC ACGCAGCTCT    2420

TTCCAGTCCA CTAGACGGTG CTCCAGACCA TATGGTATTT CCTACAATTT GTTTCAATCA    2480

ATCCTGTAAT TTGTCATCTT GGGATAGACG GAAACTGATA CAAAATGTTA TACTAGTAGA    2540

GGTTGTATTA TTACCTGATG GACATGGTCT AGTAATCTCT CCCTAACAAC TTCAAGAGAA    2600

ATGTTCTTCA AGACTTCTTC ACTCATCGTG AATGCATCTT CTTCCCATGG TTTTTTAACA    2660

GCCTGATCCA TTAAGTATTG GGAAAGATCT TTCACTCCTG ATCCCTTAAG TCCCGATATC    2720

ATGAAGTATC TAGAAAACCA AACAGGGAAA AGCACATTT CAATCAATTC GAAGACTTCC    2780

CCGGTAATTG TTTTTAAACT GAGTCTGGTA TATATATATC CACCTTTCAT ATGCCGGAAG    2840

ATCTTGGAAC TCCTCAGCAA CCTTTAATAG ATCCTTTTTC TTCTCAACCA GATCAACTTT    2900

GTTCATACAT AAAACGCGCT TTTGTTTCGG ATTTTCTTCT TCTCCCATGT ATTTGATCAA    2960

GCGTACCACT CTTGAATCGG GACTAGATAA ATCAAAGAGA AAACAGAATT CACAAACTAC    3020

AAAATAAGTC TAAGAGAACT CTATTTCTAC TTGTAATTAA TGAAAAACCA CAGTCATGAT    3080

GCCTTCTTCA AAAGAAAGAA ATAGATGTGT CTTCCCATCG GTTACGGTT CTCAAGCTT     3139

(2) INFORMATION FOR SEQ ID NO: 2:

(i) SEQUENCE CHARACTERISTICS:
        (A) LENGTH: 442 amino acids
        (B) TYPE: amino acid
        (D) TOPOLOGY: linear (ii) MOLECULE TYPE: protein (xi) SEQUENCE DESCRIPTION: SEQ ID NO: 2:

Met Asp Ser Thr Val Phe Ile Asn Asn Pro Ser Leu Thr Leu Pro Phe
1               5                   10                  15

Ser Tyr Thr Phe Thr Ser Ser Ser Asn Ser Ser Thr Thr Thr Ser Thr
                20                  25                  30

Thr Thr Asp Ser Ser Ser Gly Gln Trp Met Asp Gly Arg Ile Trp Ser
            35                  40                  45

Lys Leu Pro Pro Pro Leu Leu Asp Arg Val Ile Ala Phe Leu Pro Pro
        50                  55                  60

Pro Ala Phe Phe Arg Thr Arg Cys Val Cys Lys Arg Phe Tyr Ser Leu
65                  70                  75                  80

Leu Phe Ser Asn Thr Phe Leu Glu Thr Tyr Leu Gln Leu Leu Pro Leu
                85                  90                  95
```

```
Arg His Asn Cys Phe Leu Phe Lys His Lys Thr Leu Lys Ser Tyr
            100                 105                 110
Ile Tyr Lys Arg Gly Gly Thr Asn Asp Asp Ser Asn Lys Ala Glu
            115                 120                 125
Gly Phe Leu Phe Asp Pro Asn Glu Ile Arg Trp Tyr Arg Leu Ser Phe
            130                 135                 140
Ala Tyr Ile Pro Ser Gly Phe Tyr Pro Ser Gly Ser Gly Gly Leu
145                 150                 155                 160
Val Ser Trp Val Ser Glu Glu Ala Gly Leu Lys Thr Ile Leu Leu Cys
                165                 170                 175
Asn Pro Leu Val Gly Ser Val Ser Gln Leu Pro Pro Ile Ser Arg Pro
            180                 185                 190
Arg Leu Phe Pro Ser Ile Gly Leu Ser Val Thr Pro Thr Ser Ile Asp
            195                 200                 205
Val Thr Val Ala Gly Asp Asp Leu Ile Ser Pro Tyr Ala Val Lys Asn
            210                 215                 220
Leu Ser Ser Glu Ser Phe His Val Asp Ala Gly Gly Phe Phe Ser Leu
225                 230                 235                 240
Trp Ala Met Thr Ser Ser Leu Pro Arg Leu Cys Ser Leu Glu Ser Gly
                245                 250                 255
Lys Met Val Tyr Val Gln Gly Lys Phe Tyr Cys Met Asn Tyr Ser Pro
                260                 265                 270
Phe Ser Val Leu Ser Tyr Glu Val Thr Gly Asn Arg Trp Ile Lys Ile
                275                 280                 285
Gln Ala Pro Met Arg Arg Phe Leu Arg Ser Pro Ser Leu Leu Glu Ser
            290                 295                 300
Lys Gly Arg Leu Ile Leu Val Ala Ala Val Glu Lys Ser Lys Leu Asn
305                 310                 315                 320
Val Pro Lys Ser Leu Arg Leu Trp Ser Leu Gln Gln Asp Asn Ala Thr
                325                 330                 335
Trp Val Glu Ile Glu Arg Met Pro Gln Pro Leu Tyr Thr Gln Phe Ala
                340                 345                 350
Ala Glu Glu Gly Gly Lys Gly Phe Glu Cys Val Gly Asn Gln Glu Phe
            355                 360                 365
Val Met Ile Val Leu Arg Gly Thr Ser Leu Gln Leu Leu Phe Asp Ile
370                 375                 380
Val Arg Lys Ser Trp Leu Trp Val Pro Pro Cys Pro Tyr Ser Gly Ser
385                 390                 395                 400
Gly Gly Gly Ser Ser Gly Gly Gly Ser Asp Gly Glu Val Leu Gln Gly
            405                 410                 415
Phe Ala Tyr Asp Pro Val Leu Thr Thr Pro Val Val Ser Leu Leu Asp
            420                 425                 430
Gln Leu Thr Leu Pro Phe Pro Gly Val Cys
            435                 440

(2) INFORMATION FOR SEQ ID NO: 3:

(i) SEQUENCE CHARACTERISTICS:
        (A) LENGTH: 2554 amino acids
        (B) TYPE: nucleic acid
        (C) STRANDEDNESS: single
        (D) TOPOLOGY: linear (xi) SEQUENCE DESCRIPTION: SEQ ID NO: 3:

CGAATCAGTT AATGTGGGCG ACAAAATAAA ATCAGATTAT GTTTTATTAT TAAGTTTAGA    60
```

-continued

| | |
|---|---|
| AAGAGATGCT TCATTAAAAG TTTATGCTTT AATGTTAAAT CAGACTATTT ATTATGGGTA | 120 |
| CGACTTGTAA GCGTAATTCA AAGTTAAACA AACCTAGTTG GGAAATGGGA AGATAGATGA | 180 |
| TTTGATAAAA ACAAGACACT GTTTGGTTTC AGAGACTTCC TTTAGCATCA AAACACAAAC | 240 |
| AAAAGCGAAG CCTCTTGAGT TACTGCAAAT AGAGAATATT ATTACCCTTT TGCGACTTGT | 300 |
| CAGCTTCAGA TATTCTCACT TGTATTATTA TTTTCACGGT AAACAATGCC TTAAATAAGA | 360 |
| AACCCTGATT GGACTTTTGA TCTGACTCTA CTCTTCACTC TTTCTTCTTC TTTATTTTCA | 420 |
| GTCATGATGT CTCTCTAACC CTAATCTCAA AAAATCCAAA CTCCTTTTAT TTATTTCTAA | 480 |
| ACCTTGATTA TAGCTAGCAA TGATTAATAT AAGAATTTTT TTTCTGGATA AAGAATTAAT | 540 |
| TAGAAATTGA GTTGTAAATG TTTTGTGATG TCTAAAATTC TTTTGTTTGC AAATTAGATG | 600 |
| TAAATTGATA TATTTGAGAT TTGTATGAAA GCTAGTTTTA TTTTCCCTAA CAAGAAGTT | 660 |
| CATTATCTTG GACTTGGAGG TTTTAGAGTT TGAAAGAGTT TACAATTTAT AAGAAAAAAT | 720 |
| AATCACTATA TATATATATA TAGTGTATAT AATGAATTGT TTCACATTAA ATTGCAACAA | 780 |
| CATCAAATAA GGGTAACATA CTAACATATA GTTTGTTTGT TTACTCTTTA AAAAAGGGG | 840 |
| ATAAACTAAG AGGCTATTTT CTGCTATAAT TTAGGAACAA ACTGGATCAC ATGACAAAAA | 900 |
| TGCATCATAA TTCATATTAA ATTTTGTGTA TATCTATTTC TCATGTTTAG AAATAACATT | 960 |
| CTTGTGTGTT ATACATGTTA TCAGTTTTTC TTCCTAGATG GAAGTTTTAT TGTTGGAGTC | 1020 |
| TTTTAAAACC ATACTCACTA TGTTCCTCTT TATTTGATGT TTTGGGATTT TAGATAGGAA | 1080 |
| ATTAATAAAA AATATGTTTT CTATTTTTAT AAAATTATTT TTTTGTTAGT TTAGTAATTT | 1140 |
| TATTTTTCTT TTTTTATTAT TAGTCACAAG CAAAAATAAT AACAATATTT TTATAAAACA | 1200 |
| TTAATTTTGG TCGAACAAGT AAAAATAACT CAAAACATCA ATAATTAGA AACTAAAAAA | 1260 |
| GTAGATATTG TCAAATTTTG TGTTGAGTTC GAATAAGATA ATGTGGTCTC CTCCAACAAA | 1320 |
| ATTATTTAGA ATAAATGCAC TTCTATGACA TTAGAGAACC AACTAATTTA TTTAGAATAA | 1380 |
| AACACACATA TATATTAACA TATAAAGTAA TTCTAATTGG CTTGATATAA TATATAAGTA | 1440 |
| AAAAAATGAT CTTAATAATC TCTAGTTTTC TTGGGTTGAT CTCCACGAGT ACAATTTGAC | 1500 |
| TGACCATTAT AGAAGTTGAG AAGCGTGCAT GTAATAAAAG TTGTATATTA CAAATTAGAG | 1560 |
| AGGAAAAAGA AAGAAAGAAA AAAGATTTGA AGATGTGATC AAGTGTGAAA AGTATTGGAG | 1620 |
| TAGTCTCCAA ATTAATAATT TCGATGCTGG GCATTGACAA GATAACTCTG AAGCTCTCAA | 1680 |
| CTTTAAGACC ATCACTTCCT CTCCACCATT TTCACGTTTA CCCAAACACA CACATATACA | 1740 |
| AACAAAATTT TGTTAGTCAA TAATTATCAC CAAACTGGGG TTATAACAAG GCTTTTGGAT | 1800 |
| ACTTGTGCTT GTTGATGTTC TAGGTTCGTA TGATAACAAA GTACATCCGT TATATATATT | 1860 |
| CGAAACACAC TTTAATATTA AAAATATATA TCCAATTTTC TTGTGAAATT TAGATTATTT | 1920 |
| GGAATTAAAC CTATTTCTCT TGTCTTGGCC ACTTGACCGG TTTAGTTTTT TAGACGTATT | 1980 |
| TTATTATTTC TGTTTAGAAA ATAACAACAT ATATCAACTG ATTTTTTACT TCCAATCTCT | 2040 |
| TTTTGTCAGC ACACAAATAG AAAAACGTCT GTAAGCTAAG CTATCAACTA AAACATTAAC | 2100 |
| ATATATAATC TTTTACGTTG ATAGAAAATA AACATAAATT TCTGAGTTAT TTTTTTTTTG | 2160 |
| GTTGGTGTGT CACTACTTAC TTACTACTAT ACCTTTTTAA CAATAAAGAA ACACTATTTC | 2220 |
| TTTTTCTATT CAATATAATA TATGTTTTCT ATTTGTATAA ATCCATTACC TTTGTTTGTT | 2280 |
| TTATACCAAA TGTTCTTTAT ATATAGTATA TGCGACGTTA CTCTATTGAA GTCAAGAACA | 2340 |
| TATCAAAAAC CCATGCAAGA AGCTCACAGA GAAAGACGAA ACGCTTTTGT CTCTTTCTTC | 2400 |

```
AAAACTTTTA CATATGATCT TTGCCTCTTT TCCTACAATG GGTTTTGCAT AACTTTCACC    2460

AAAACCCTCC TCAAAAGCCC TTCACATATT CCCAACACAA GAAATAAAC TCTAAATCCA     2520

CTTTCACCAA ATCTTTTCAT TTTTCAGCTA AAATG                               2555
```

(2) INFORMATION FOR SEQ ID NO: 4:

(i) SEQUENCE CHARACTERISTICS:
        (A) LENGTH: 442 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 4:

```
Met Asp Ser Thr Val Phe Ile Asn Asn Pro Ser Leu Thr Leu Pro Phe
1               5                   10                  15

Ser Tyr Thr Phe Thr Ser Ser Asn Ser Ser Thr Thr Thr Ser Thr
            20                  25                  30

Thr Thr Asp Ser Ser Ser Gly Gln Trp Met Asp Gly Arg Ile Trp Ser
        35                  40                  45

Lys Leu Pro Pro Pro Leu Leu Asp Arg Val Ile Ala Phe Leu Pro Pro
50                  55                  60

Pro Ala Phe Phe Arg Thr Arg Cys Val Cys Lys Arg Phe Tyr Ser Leu
65                  70                  75                  80

Leu Phe Ser Asn Thr Phe Leu Glu Thr Tyr Leu Gln Leu Leu Pro Leu
                85                  90                  95

Arg His Asn Cys Phe Leu Phe Phe Lys His Lys Thr Leu Lys Ser Tyr
                100                 105                 110

Ile Tyr Lys Arg Gly Gly Thr Asn Asp Asp Ser Asn Lys Ala Glu
            115                 120                 125

Gly Phe Leu Phe Asp Pro Asn Glu Ile Arg Trp Tyr Arg Leu Ser Phe
            130                 135                 140

Ala Tyr Ile Pro Ser Gly Phe Tyr Pro Ser Gly Ser Ser Gly Gly Leu
145                 150                 155                 160

Val Ser Trp Val Ser Glu Glu Ala Gly Leu Lys Thr Ile Leu Leu Cys
                165                 170                 175

Asn Pro Leu Val Gly Ser Val Ser Gln Leu Pro Pro Ile Ser Arg Pro
            180                 185                 190

Arg Leu Phe Pro Ser Ile Gly Leu Ser Val Thr Pro Thr Ser Ile Asp
            195                 200                 205

Val Thr Val Ala Gly Asp Asp Leu Ile Ser Pro Tyr Ala Val Lys Asn
210                 215                 220

Leu Ser Ser Glu Ser Phe His Val Asp Ala Gly Phe Phe Ser Leu
225                 230                 235                 240

Trp Ala Met Thr Ser Ser Leu Pro Arg Leu Cys Ser Leu Glu Ser Gly
                245                 250                 255

Lys Met Val Tyr Val Gln Gly Lys Phe Tyr Cys Met Asn Tyr Ser Pro
            260                 265                 270

Phe Ser Val Leu Ser Tyr Glu Val Thr Gly Asn Arg Trp Ile Lys Ile
            275                 280                 285

Gln Ala Pro Met Arg Arg Phe Leu Arg Ser Pro Ser Leu Leu Glu Ser
        290                 295                 300

Lys Gly Arg Leu Ile Leu Val Ala Ala Val Glu Lys Ser Lys Leu Asn
305                 310                 315                 320
```

-continued

```
Val Pro Lys Ser Leu Arg Leu Trp Ser Leu Gln Gln Asp Asn Ala Thr
            325                 330                 335

Trp Val Glu Ile Glu Arg Met Pro Gln Pro Leu Tyr Thr Gln Phe Ala
            340                 345                 350

Ala Glu Glu Gly Gly Lys Gly Phe Glu Cys Val Gly Asn Gln Glu Phe
            355                 360                 365

Val Met Ile Val Leu Arg Gly Thr Ser Leu Gln Leu Leu Phe Asp Ile
    370                 375                 380

Val Arg Lys Ser Trp Leu Trp Val Pro Pro Cys Pro Tyr Ser Gly Ser
385                 390                 395                 400

Gly Gly Gly Ser Ser Gly Gly Gly Ser Asp Gly Glu Val Leu Gln Gly
                405                 410                 415

Phe Ala Tyr Asp Pro Val Leu Thr Thr Pro Val Val Ser Leu Leu Asp
            420                 425                 430

Gln Leu Thr Leu Pro Phe Pro Gly Val Cys
            435                 440
```

(2) INFORMATION FOR SEQ ID NO: 5:

(i) SEQUENCE CHARACTERISTICS:
        (A) LENGTH: 164 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 5:

```
Glu Ala Phe Gln Thr Ile Phe Asn Leu Pro Gly Thr Thr Pro Thr Ile
1               5                   10                  15

Asn Leu Gln Asn Met Ile Met Thr Thr Asn Cys Arg Gln Lys Ile Ile
            20                  25                  30

Cys Ser Ser Trp Ile Thr Leu His Ala Ser Ile Trp Met Gln Gln Ser
            35                  40                  45

Ile His His Asn Asn Ser Ala Arg Pro Thr Tyr Tyr Gln Thr Leu
    50                  55                  60

Lys Ile Pro Leu Pro Ser Ala Ser Leu Ile Cys Asp Ser Pro Asn Ser
65                  70                  75                  80

Thr Asn Thr Ala Ile Ser Thr Leu Glu Cys Thr Thr Ile Asn Ser Ile
            85                  90                  95

Ser Phe Thr Ile Val Tyr Ile Asn Thr Arg His Arg Asp Ile Ser Leu
            100                 105                 110

Gln Cys Thr Val Lys Ala Glu Cys Gly Thr Ile Gln Ile Glu Ile Arg
            115                 120                 125

Ser Ala His Ala Val Leu Ile Ser Tyr Asp Lys Ala Val Met Phe Cys
            130                 135                 140

Gln Val Val Asp Asp Glu His Glu Arg Ala Val Ile Thr Pro Glu Gln
145                 150                 155                 160

Ser Phe Thr Ala
```